US012599632B2

(12) United States Patent
Kihoin et al.

(10) Patent No.: US 12,599,632 B2
(45) Date of Patent: Apr. 14, 2026

(54) THERAPEUTIC AGENT FOR NERVE DISORDERS

(71) Applicant: Neurotech Medical Co., Ltd., Toyonaka (JP)

(72) Inventors: Nagatoshi Kihoin, Osaka (JP); Kunihiko Okada, Osaka (JP)

(73) Assignee: Neurotech Medical Co., Ltd., Osaka (JP)

( * ) Notice: Subject to any disclaimer, the term of this patent is extended or adjusted under 35 U.S.C. 154(b) by 325 days.

(21) Appl. No.: 18/254,745

(22) PCT Filed: Nov. 30, 2021

(86) PCT No.: PCT/JP2021/043813
§ 371 (c)(1),
(2) Date: May 26, 2023

(87) PCT Pub. No.: WO2022/114216
PCT Pub. Date: Jun. 2, 2022

(65) Prior Publication Data
US 2024/0033296 A1    Feb. 1, 2024

(30) Foreign Application Priority Data
Nov. 30, 2020    (JP) ................................. 2020-198046

(51) Int. Cl.
| *A61K 35/28* | (2015.01) |
| *A61K 9/00* | (2006.01) |
| *A61K 9/19* | (2006.01) |
| *A61P 25/00* | (2006.01) |

(52) U.S. Cl.
CPC ............ *A61K 35/28* (2013.01); *A61K 9/0019* (2013.01); *A61K 9/0043* (2013.01); *A61K 9/19* (2013.01); *A61P 25/00* (2018.01)

(58) Field of Classification Search
CPC ..................................................... A61K 35/28
See application file for complete search history.

(56) References Cited

U.S. PATENT DOCUMENTS

| 9,109,206 B2 | 8/2015 | Sabaawy |
| 2013/0195991 A1 | 8/2013 | Ueda et al. |
| 2019/0117700 A1 | 4/2019 | Honmou et al. |

FOREIGN PATENT DOCUMENTS

| CA | 3033408 A1 | 1/2018 | |
| CA | 3200384 A1 | 6/2022 | |
| CN | 108753708 A * | 11/2018 | ............. C07K 14/52 |
| JP | 2004167202 A | 6/2004 | |
| JP | 4061487 B2 | 3/2008 | |
| JP | 2008137954 A | 6/2008 | |
| JP | 2013508013 A | 3/2013 | |
| JP | 2016065106 A | 4/2016 | |
| JP | 6296622 B2 | 3/2018 | |
| JP | 2019527218 A | 9/2019 | |
| KR | 1020080049562 A | 6/2008 | |
| KR | 1020170084731 A | 7/2017 | |
| WO | WO 2011046570 A1 | 4/2011 | |
| WO | WO 2011118795 A1 | 9/2011 | |
| WO | WO 2014/141219 A1 | 9/2014 | |
| WO | WO 2015/152656 A1 | 10/2015 | |
| WO | WO 2016/153114 A1 | 9/2016 | |
| WO | WO 2017188457 A1 | 11/2017 | |
| WO | WO-2017214707 A1 * | 12/2017 | ........... C12N 5/0665 |
| WO | WO 2018015945 A2 | 1/2018 | |

OTHER PUBLICATIONS

Lee, J. Y. et al., "Combination of Human Mesenchymal Stem Cells and Repetitive Transcranial Magnetic Stimulation Enhances Neurological Recovery of 6-Hydroxydopamine Model of Parkinsonian's Disease." Tissue Engineering and Regenerative Medicine. Jan. 2020, vol. 17, No. 1, pp. 67-80 abstract, p. 69, right col. 2.3 to p. 69, right column, pp. 6-7, fig. 1, p. 71, right col. 3.2, table 1, Published on Jan. 22, 2020.

Yusuke Sakiyama et al., "Review/Advances in Neurological Therapeutics (2018). Spinocerebellar degeneration."Neurological Therapeutics 2019, vol. 36, No. 5 , pp. 580-583 p. 580, left column section I to p. 581, right column. section III, Published on Jun. 2, 2020.

Bucan , V. et al., "Effect of Exosomes from Rat Adipose-Derived Mesenchymal Stem Cells on Neurite Outgrowth and Sciatic Nerve Regeneration After Crush Injury." Molecular Neurobiology, 2019, vol. 56, pp. 1812-1824 abstract, fig. 3, 5, Published on Jun. 21, 2018.

Moretti, D. V. "Available and future treatments for atypical parkinsonism. A systematic review." CNS Neuroscience and Therapeutics. 2019, vol. 25, No. 2, pp. 159-174 abstract, Published on Oct. 7, 2018.

Chol, Y-K. et al., "Combined effect of pulsed electromagnetic field and sound wave on In Vitro and In Vivo neural differentiation of human mesenchymal stem cells." Biotechnology Progress. 2017, vol. 33, No. 1, pp. 201-211 entire text, Published on Nov. 18, 2016.

Choi, Y-K. et al., "Stimulation of sub-sonic vibration promotes the differentiation of adipose tissue-derived mesenchymal stem cells into neural cells." Life Sciences. 2012, vol. 91, No. 9-10, pp. 329-337 entire text, Published on Jul. 31, 2012.

(Continued)

*Primary Examiner* — Qiuwen Mi
(74) *Attorney, Agent, or Firm* — HoustonHogle LLP

(57) ABSTRACT

The present invention addresses the problem of providing a therapeutic agent that is more efficacious for treating nerve disorders, said therapeutic agent comprising a culture supernatant of mesenchymal stem cells. The present invention provides a therapeutic agent for nerve disorders, said therapeutic agent comprising a culture supernatant of mesenchymal stem cells and/or cells capable of differentiating into mesenchymal stem cells and being to be used together with stimulation of patient's nerves, wherein the stimulation is preferentially provided to one or more sites selected from the group consisting of a site of nerve damage, an area surrounding a site of nerve damage, and a site compensating for the function of a site of nerve damage.

18 Claims, No Drawings

(56)                    References Cited

OTHER PUBLICATIONS

Extended European Search Report issued Oct. 8, 2024 in EP Patent Application No. 21898187.6 Nine pages.

De Gregorio, C. et al. "Human adipose-derived mesenchymal stem cell-conditioned medium ameliorates polyneuropathy and foot ulceration in diabetic BKS db/db mice", Stem Cell Research & Therapy, vol. 11, No. 1, May 1, 2020 (May 1, 2020), pp. 168-168, XP93203962, London, UK.

Giampà, C et al., "Conditioned medium from amniotic cells protects striatal degeneration and ameliorates motor deficits in the R6/2 mouse model of Huntington's disease", Journal of Cellular and Molecular Medicine, vol. 23, No. 2, pp. 1581-1592, XP093203943 (2018) Retrieved from the Internet: URL:https://api.wiley.com/onlinelibrary/tdm/v1/articles/10.1111%2Fjcmm.14113.

Wang, F. et al., "Synergistic Effects of Mesenchymal Stem Cell Transplantation and Repetitive Transcranial Magnetic Stimulation on Promoting Autophagy and Synaptic Plasticity in Vascular Dementia", The Journals of Gerontology Series A: Biological Sciences and Medical Sciences, vol. 74, No. 9, Sep. 25, 2018 (Sep. 25, 2018), pp. 1341-1350, XP093145599.

Yang, C. et al., "Synergistic effect of electric stimulation and mesenchymal stem cells against Parkinson's disease", Aging, vol. 12, No. 16, Aug. 24, 2020 (Aug. 24, 2020), pp. 16062-16071, XP93203955.

Choi, Y-K. et al., "Combined effect of pulsed electromagnetic field and sound wave on In Vitro and In Vivo neural differentiation of human mesenchymal stem cells." Biotechnology Progress. 2017, vol. 33, No. 1, pp. 201-211 entire text, Published on Nov. 18, 2016.

Japanese Office Action-Notice of reasons for refusal, mailed on Dec. 20, 2024, from Japanese Application No. 2020-198046, filed on Nov. 30, 2020. 8 pages.

Drago, D., et al., "The stem cell secretome and its role in brain repair", Elsevier, Biochimie 95 (12) :2271-2285 (2013).

Mita, T., et al., "Potential for the Treatment of Alzheimer's Disease Using Cultured Supernatant Derived from Deciduous Dental Pulp Stem Cells" Regenerative Medicine, Official Journal of the Japanese Society for Regenerative Medicine, 12: F-1-4 ( 2013).

Shimojima, C., et al., "Conditioned Medium from the Stem Cells of Human Exfoliated Deciduous Teeth Ameliorates Experimental Autoimmune Encephalomyelitis", The Journal of Immunology, 196 (10): 4164-4171 (2016).

Ueda, M., "Organ regeneration using stem cell culture medium", The 37th Annual Meeting of the Japanese Society of Blood Programme/Symposium 3, 4(36): 841-844 (2014).

International Search Report and Written Opinion of the International Searching Authority, mailed on Jan. 25, 2022, from International Application No. PCT/JP2021/043813, filed on Nov. 30, 2021. 17 pages.

International Preliminary Report on Patentability, mailed on Jun. 15, 2023, from International Application No. PCT /JP2021 /043813, filed on Nov. 30, 2021. 13 pages.

US Office Action, mailed on Oct. 8, 2025, from U.S. Appl. No. 18/007,076, filed Jan. 27, 2023. 26 pages.

Chinese Second Office Action, mailed on Mar. 22, 2025, from Chinese Application No. 202180058631.7, filed on Jul. 30, 2021. 14 pages.

Extended European Search Report, mailed on Aug. 1, 2024, from European Application No. 21849087.8, filed on Jul. 30, 2021. 16 pages.

International Search Report and Written Opinion of the International Searching Authority, mailed on Aug. 24, 2021, from International Application No. PCTJP2021028420, filed on Jul. 30, 2021. 7 pages.

International Preliminary Report on Patentability, mailed on Feb. 9, 2023, from International Application No. PCTJP2021028420, filed on Jul. 30, 2021. 9 pages.

Isakovic, J., et al., "Mesenchymal stem cell therapy for neurological disorder: The light or the dark side of the force?", Frontier in Bioengineering and Biotechnology, 11:1-30 (2023).

Ito, A., et al., "Regenerative Rehabilitation for Stroke Recovery by Inducing Synergistic Effects of Cell Therapy and Neurorehabilitation on Motor Function: A Narrative Review of Pre-Clinical Studies", International Journal of Molecular Sciences, MDPI, 21(3135): 1-21 (2020).

Kamelska_Sadowska, A. M., et al., "Review of the Current Knowledge on the Role of Stem Cell Transplantation in Neurorehabilitation", BioMed Research International, 1-9 (2019).

Song, Y., et al., "Management of perinatal care of high-risk infants", Beijing People's Military Medical Publishing House, pp. 354-355 (2012).

Zhao, K., et al., "Combination of mild therapeutic hypothermia and adipose-derived stem cells for ischemic brain injury", Neural Regeneration Research, 1759-1770 (2018).

Zhou, L., et al., "Theory and Practice of Motor Human Sciences vol. II", China National Library of Publications, (2016).

Chen, G., et al., "Clinical Cell Therapy Q&A", People's Military Medical Publishing House, p. 118, (2011).

Decision of Refusal mailed on Jan. 28, 2025, from CN Patent Application No. 202180058631.7, filed on Jan. 30, 2023. 23 pages.

* cited by examiner

THERAPEUTIC AGENT FOR NERVE DISORDERS

RELATED APPLICATIONS

This application is a § 371 National Phase Application of International Application No. PCT/JP2021/043813, filed on Nov. 30, 2021, now International Publication No. WO 2022/114216 A1, published on Jun. 2, 2022, which International Application claims priority to Japanese Application 2020-198046, filed on Nov. 30, 2020, both of which are incorporated herein by reference in their entirety.

TECHNICAL FIELD

The present invention relates to a therapeutic agent for nerve disorders.

BACKGROUND ART

Mesenchymal stem cells and culture supernatants thereof are applied as therapeutic agents for various diseases.

Patent Literature 1 and Patent Literature 2 describe that a combined use of the administration of mesenchymal stem cells and rehabilitation can improve the therapeutic effect on neurologic disorders, etc.

Patent Literature 3 describes a treatment for injury sites using a culture supernatant of stem cells obtained by serum-free culture of dental pulp stem cells.

Patent Document 1: PCT International Publication No. WO2017/188457

Patent Document 2: Japanese Unexamined Patent Application (Translation of PCT Application), Publication No. 2013-508013

Patent Document 3: Japanese Patent No. 6296622

DISCLOSURE OF THE INVENTION

Problems to be Solved by the Invention

However, there is a further need to improve the therapeutic effect on nerve disorders.

The present invention has been made in view of the above circumstances, and an objective of the present invention is to provide a therapeutic agent containing a culture supernatant of mesenchymal stem cells, which is more effective for treatment of nerve disorders.

Means for Solving the Problems

The present inventors have discovered that the above problems can be solved by administration of a culture supernatant of mesenchymal stem cells and/or cells capable of differentiating into mesenchymal stem cells in combination with stimulation of a nerve of a patient, and adjusting the timing of applying the stimulation and the site to be stimulated, and thus have completed the present invention. More specifically, the present invention provides the following (1) to (7).

(1) A therapeutic agent for a nerve disorder, wherein the therapeutic agent contains a culture supernatant of mesenchymal stem cell and/or a cell capable of differentiating into a mesenchymal stem cell, and is used in combination with stimulation of a nerve of a patient, and the stimulation is preferentially applied to one or more sites selected from the group consisting of a nerve injury site, an area surrounding the nerve injury site, and a site compensating for the function of the nerve injury site.

(2) A therapeutic agent for nasal administration for a nerve disorder, wherein the therapeutic agent contains a culture supernatant of a mesenchymal stem cell and/or a cell capable of differentiating into a mesenchymal stem cell, and is used in combination with stimulation of a nerve of a patient, and the stimulation is performed between before and 16 hours after administration of the therapeutic agent.

(3) A therapeutic agent for intravenous administration for a nerve disorder, wherein the therapeutic agent contains a culture supernatant of a mesenchymal stem cell and/or a cell capable of differentiating into a mesenchymal stem cell, and is used in combination with stimulation of a nerve of a patient, and the stimulation is performed between before and 3 hours after administration of the therapeutic agent.

(4) A therapeutic agent for subcutaneous administration for a nerve disorder, wherein the therapeutic agent contains a culture supernatant of a mesenchymal stem cell and/or a cell capable of differentiating into a mesenchymal stem cell, and is used in combination with stimulation of a nerve of a patient, and the stimulation is performed between before and 16 hours after administration of the therapeutic agent.

(5) The therapeutic agent according to any one of (1) to (4), wherein the stimulation is one or more kinds of stimulation selected from the group consisting of motor stimulation, sensory stimulation, electrical stimulation, magnetic stimulation, verbal stimulation, and higher brain function stimulation.

(6) The therapeutic agent according to any one of (1) to (5), wherein the culture supernatant is not diluted or concentrated in terms of soluble solid content.

(7) The therapeutic agent according to any one of (1) to (5), wherein a lyophilizate of the culture supernatant is dissolved and then used at the time of administration.

Effects of the Invention

According to the present invention, a therapeutic agent containing a culture supernatant of mesenchymal stem cells, which is more effective for treatment of nerve disorders, is provided.

PREFERRED MODE FOR CARRYING OUT THE INVENTION

Hereinafter, the embodiments of the present invention will be described, but the present invention is not limited thereto.

<Therapeutic agent> The therapeutic agent for nerve disorders of the present invention (hereinafter, also referred to as "the therapeutic agent of the present invention") is a preparation containing a culture supernatant of mesenchymal stem cells and/or cells capable of differentiating into mesenchymal stem cells, and, is used in combination with stimulation of a nerve of a patient. The modes of use of the therapeutic agent include the following 4 modes. The therapeutic agent of the present invention may be provided with any one of the following 4 modes, and may also be provided with mode 1 and any one of modes 2 to 4 in combination.

(Mode 1) Mode 1 involves preferentially stimulating one or more sites selected from the group consisting of a nerve injury site, an area surrounding the nerve injury site, and a site compensating for the function of the nerve injury site.

(Mode 2) Mode 2 involves, when the preparation is the therapeutic agent for nasal administration, performing stimulation between before and 16 hours after administration of the therapeutic agent.

(Mode 3) Mode 3 involves, when the preparation is the therapeutic agent for intravenous administration, performing stimulation between before and 3 hours after administration of the therapeutic agent.

(Mode 4) Mode 4 involves, when the preparation is the therapeutic agent for subcutaneous administration, performing stimulation between before and 16 hours after administration of the therapeutic agent.

It has been conventionally known that a culture supernatant of stem cells can be useful for treatment of neurologic disorders, and the like (for example, Patent Literature 3). However, as a result of the study, the present inventors have discovered that a combined use of administration of a culture supernatant of mesenchymal stem cells and/or cells capable of differentiating into mesenchymal stem cells, and simulation of a nerve of a patient particularly enhances the therapeutic effect.

Further, the present inventors have also discovered an unexpected finding such that if stimulation of a nerve of a patient is preferentially applied to one or more sites selected from the group consisting of a nerve injury site, an area surrounding the nerve injury site, and a site compensating for the function of the nerve injury site, the resulting therapeutic effect is particularly high.

Furthermore, the present inventors have also discovered an unexpected finding such that the therapeutic effect can be further enhanced by adjusting the timing of applying stimulation depending on the route of administration of the culture supernatant.

The reason why the present invention enhances the therapeutic effect on nerve disorders is inferred that adjustments of the site to be simulated and/or the timing to applying stimulation as described above facilitates the transfer of active ingredients and the like contained in the culture supernatant to the affected area (nerve injury site etc.), so as to accelerate the effect exhibited by the culture supernatant.

The term "nerve disorders" used herein refers to any disorder of damaging a nerve itself, or the function thereof, and the underlying diseases thereof, the site of nerve injury and the like are not particularly limited.

Examples of the diseases that cause nerve disorders are not particularly limited, and include arbitrary selected diseases causing nerve disorders. Examples of these diseases include cerebrovascular disease, brain tumor, encephalitis, dementia, neurodegenerative diseases, spinal cord injury, myelitis, hernia of the intervertebral disk, and, other central nervous system disorders, and peripheral nerve disorders.

The term "treatment for nerve disorders" used herein means that various symptoms associated with nerve disorders (movement disorder, articulation disorder, swallowing disorder, higher brain dysfunction, dementia, aphasia, Parkinson's syndrome, ataxia, sensory disorder, pain, coldness, numbness, burning, etc.) are alleviated or completely cured. Whether or not the therapeutic effect on nerve disorders was exhibited is evaluated based on known standards and methods such as the NIHSS (National Institutes of Health Stroke Scale), mRS (modified Rankin Scale), AIS (ASIA Impairment Scale), Frankel Classification, SIAS (Stroke Impairment Assessment), BRS (Brunnstrom stage), FMA (Fugl Meyer Assessment), MMT (Manual Muscle Testing), FMA (Fugl Meyer Assessment), the Standard Language Test of Aphasia (SLTA), WAB Western Aphasia Battery, Token Test, and MMSE (Mini-Mental State Examination).

The term "patient" used herein refers to any organism that has developed a nerve disorder. Examples thereof include mammals such as humans, monkeys, cows, horses, pigs, dogs and cats, birds or reptiles, and any other pet animals.

Hereinafter, the composition of the therapeutic agent of the present invention will be described in detail.

(Culture supernatant of mesenchymal stem cells, cells capable of differentiating into mesenchymal stem cells) The therapeutic agent of the present invention contains culture supernatant of mesenchymal stem cells and/or cells capable of differentiating into mesenchymal stem cells (hereinafter, may also be referred to as "the culture supernatant in the present invention"). The therapeutic agent of the present invention may also contain both a culture supernatant of mesenchymal stem cells, and a culture supernatant of cells capable of differentiating into mesenchymal stem cells, or may contain either one of them. When the therapeutic agent of the present invention contains both a culture supernatant of mesenchymal stem cells, and a culture supernatant of cells capable of differentiating into mesenchymal stem cells, the mixing ratio of them is not particularly limited, and is adjusted as appropriate depending on the therapeutic effect and the like to be obtained.

As long as mesenchymal stem cells (MSC) used herein are derived from the mesenchyme and are somatic stem cells capable of autonomous replication and differentiation, a method for preparing MSCs and the tissue and the like from which the MSCs are derived are not particularly limited.

The term "cells capable of differentiating into mesenchymal stem cells" used herein refers to cells capable of differentiating into mesenchymal stem cells usually through division and replication. Such cells have both self-replication ability and totipotency with which cells can differentiate into various cells. Examples of cells capable of differentiating into mesenchymal stem cells include IPS cells (Induced Pluriopotent Stem Cells) and ES cells (Embryonic Stem Cells).

Mesenchymal stem cells and cells capable of differentiating into mesenchymal stem cells may be those isolated from bone marrow, fat, dental pulp, blood (peripheral blood, umbilical cord blood, etc.), placenta, umbilical cord, and other tissues in vivo.

Mesenchymal stem cells and cells capable of differentiating into mesenchymal stem cells may be those derived from the cells (autologous cells) of the patient to be subject of administration, or may be those derived from cells (allogeneic cells) other than the cells of the patient.

Mesenchymal stem cells may be cells induced to differentiate from ES cells, cells induced to differentiate from induced pluripotent stem cells (iPS cells, etc.), established cells, Muse cells (Multi-lineage differentiating Stress Enduring Cell), and the like.

As mesenchymal stem cells, cells showing negative for a differentiation marker (CD24 or the like) and those maintaining an undifferentiated state are usually used.

Mesenchymal stem cells may be cells for which the expression of various markers satisfies any one of the following.

Positive for at least one marker selected from CD73, CD90, CD105, and CD200.

Negative for at least one marker selected from CD19, CD34, CD45, CD74, CD79a, and HLA-DR.

Mesenchymal stem cells are preferably positive for two or more of CD73, CD90, CD105, and CD200, and negative for four or more of CD19, CD34, CD45, CD74, CD79a, and HLA-DR, and more preferably positive for CD73, CD90, CD105, and CD200, and negative for CD19, CD34, CD45, CD74, CD79a, and HLA-DR.

Examples of mesenchymal stem cells include mesenchymal stem cells that have been reported to be applicable for treatment of various diseases, such as mesenchymal stem cells described in International Publication No. WO2017/188457, International Publication No. WO2009/002503, Japanese Translation of PCT International Application Publication No. 2013-508013, and the like.

A method for preparing mesenchymal stem cells is not particularly limited, and any method known as a method for preparing mesenchymal stem cells can be employed. An example of a preferable preparation method is the method described in Japanese Patent No. 4061487. This method involves a step of adding fresh bone marrow cells to a culture dish and adhering these cells to the culture dish for proliferation, and a step of re-growing a part of the obtained cells on the culture dish, and the like.

The culture supernatant in the present invention is obtained by culturing the above mesenchymal stem cells and/or cells capable of differentiating into mesenchymal stem cells.

When the culture supernatant in the present invention is obtained, a medium to be used and culture conditions are not particularly limited, and can be selected as appropriate depending on the type and the like of mesenchymal stem cells or cells capable of differentiating into mesenchymal stem cells.

Examples of a medium to be used for culturing mesenchymal stem cells and/or cells capable of differentiating into mesenchymal stem cells include DMEM medium, RPMI1640 medium, HamF12 medium, and combinations thereof. The medium may contain ingredients (various sera, bovine serum albumin, antibiotics, vitamins, minerals, etc.) to be used for culturing stem cells.

After culturing mesenchymal stem cells and/or cells capable of differentiating into mesenchymal stem cells, cells from the obtained culture are appropriately treated as necessary, and then the culture supernatant in the present invention is obtained. Examples of such treatment include generally known steps such as removal of cells (via filtration or the like), concentration, freezing, drying, and dilution.

The culture supernatant in the present invention is preferably obtained by removing cells from the culture of mesenchymal stem cells and/or cells capable of differentiating into mesenchymal stem cells.

The present inventors have discovered that when the soluble solid contents (the content of active ingredients (protein, etc.)) in culture supernatants remain constant, the lower the gross amount of the culture supernatant (the higher the concentration of the soluble solid content), the more easily the effect of the present invention is exhibited. Therefore, the culture supernatant in the present invention is preferably one undiluted (with medium, physiological saline, etc.) in terms of the soluble solid content after culturing of mesenchymal stem cells and/or cells capable of differentiating into mesenchymal stem cells, or the one concentrated (by ultrafiltration or the like) in terms of the soluble solid content after the same. The soluble solid content is not particularly limited, but may range from 0.02 mg/mL to 200 mg/mL.

Commercially available kits may be used for isolating and culturing mesenchymal stem cells and/or cells capable of differentiating into mesenchymal stem cells.

In the case of the therapeutic agent of the present invention, the dose and the frequency of administration of the culture supernatant in the present invention can be appropriately adjusted depending on the effect to be desired and the situation (age, body weight, degree of symptom, etc.) of the patient to be subject of administration.

In the case of the therapeutic agent of the present invention, the time required for each administration can be adjusted depending on the method for administering the culture supernatant in the present invention, the frequency of administration, and the like.

The frequency of carrying out the combination of administration of the culture supernatant and stimulation according to the present invention is not particularly limited, but each may be carried out once or repeatedly twice or more. When the combination is repeatedly performed twice or more, it may be performed for several weeks (for example, one week) or more to several months (for example, 36 months). The instances of administration of the culture supernatant and the instances of stimulation applied may be the same or different.

(Form of therapeutic agent) The therapeutic agent of the present invention may contain conventionally known ingredients depending on the administration method and the like.

The therapeutic agent of the present invention can be any one of a therapeutic agent for nasal administration, a therapeutic agent for intravenous administration, and a therapeutic agent for subcutaneous administration.

When the therapeutic agent of the present invention is a therapeutic agent for nasal administration, a medium (a physiological buffer solution, sterile water, a physiological saline solution, a glucose solution, a medium) and an ingredient(s) (an emulsifying agent, a surfactant, a stabilizer, etc.) known to be blended in the composition of therapeutic agent for nasal administration may be blended as necessary, together with the culture supernatant in the present invention.

When the therapeutic agent of the present invention is a therapeutic agent for intravenous administration, a medium (a physiological buffer solution, sterile water, a physiological saline solution, a glucose solution, a medium) and an ingredient(s) (an emulsifying agent, a surfactant, a stabilizer, etc.) known to be blended in the composition of therapeutic agent for intravenous administration may be blended as necessary, together with the culture supernatant in the present invention. When the therapeutic agent of the present invention is a therapeutic agent for intravenous administration, it is usually administered via injection or infusion.

When the therapeutic agent of the present invention is a therapeutic agent for subcutaneous administration, a medium (a physiological buffer solution, sterile water, a physiological saline solution, a glucose solution, a medium) and an ingredient(s) (an emulsifying agent, a surfactant, a stabilizer, etc.) known to be blended in the composition of therapeutic agent for subcutaneous administration may be blended as necessary, together with the culture supernatant in the present invention.

A method for preserving the therapeutic agent of the present invention is not particularly limited, and examples thereof include cryopreservation, freeze-drying, and refrigerated storage.

The cryopreserved therapeutic agent is thawed and then used for treatment. The freeze-dried therapeutic agent is dissolved in a medium (a physiological buffer solution, sterile water, a physiological saline solution, a glucose solution, a medium) and then used for treatment.

The therapeutic agent of the present invention preferably contains a solution in which a freeze-dried product of the culture supernatant in the present invention has been dissolved. Examples of the solvent of the solution include a physiological buffer solution, sterilized water, a physiological saline solution, a glucose solution, and a medium.

The therapeutic agent of the present invention may be subdivided into containers (vials, etc.) each containing a single dose or multiple doses.

From the viewpoint of convenience and the like, the culture supernatant in the present invention is preferably cryopreserved in a state of being subdivided into containers each containing one or more doses.

(Stimulation) The therapeutic agent of the present invention is used in combination with stimulation of a nerve of a patient, and the stimulation satisfies one of the following four requirements, or a combination of requirement 1 and any one of requirements 2 to 4.

(Requirement 1) Stimulation is preferentially applied to one or more sites selected from the group consisting of a nerve injury site, an area surrounding the nerve injury site, and a site compensating for the function of the nerve injury site.

(Requirement 2) When the preparation is a therapeutic agent for nasal administration, stimulation is performed between before and 16 hours after administration of the therapeutic agent.

(Requirement 3) When the preparation is a therapeutic agent for intravenous administration, stimulation is performed between before and 3 hours after administration of the therapeutic agent.

(Requirement 4) When the preparation is a therapeutic agent for subcutaneous administration, stimulation is performed between before and 16 hours after administration of the therapeutic agent.

When the rate of blood flow or the like to an affected area increases, or the metabolic rate in the affected area increases while the administered culture supernatant in the present invention remains in or around the affected area (a nerve injury site of the brain or the like), the culture supernatant in the present invention is transferred to the affected area, and thus the therapeutic effect can be efficiently enhanced. The specific techniques are the above requirements 1 to 4.

When the therapeutic agent of the present invention is used in a form satisfying the above requirement 1, stimulation (motor stimulation, sensory stimulation, electrical stimulation, magnetic stimulation, verbal stimulation, and higher brain function stimulation etc., described later) is applied at an arbitrary timing (preferably the timing satisfying any one of requirements 2 to 4). By applying stimulation so as to satisfy the above requirement 1, the blood flow rate in the affected area (nerve injury site, etc.) and the metabolic rate in the same area increase preferentially over the other nerve areas. Hence, the amount of the culture supernatant in the invention, which is transferred to the affected area, can be increased.

When the therapeutic agent of the present invention is used in a form satisfying any one of the above requirements 2 to 4, stimulation (whole-body exercise, local exercise, or motor stimulation, sensory stimulation, electrical stimulation, magnetic stimulation, verbal stimulation, and higher brain function stimulation, etc., described later) is performed within the administration period specified in these requirements of the therapeutic agent. By performing stimulation so as to satisfy any one of the above requirements 2 to 4, the rate of blood flow to the affected area (brain, etc.) increases and/or the metabolic rate in the affected area increases at the timing when the residual amount of the culture supernatant in the present invention in blood or a cerebrospinal fluid is high. Hence, the amount of the culture supernatant in the present invention to be transferred to the affected area can be increased.

In the above requirements 2 to 4, the expression "stimulation is performed before administration of the therapeutic agent" means that the time point of initiating the stimulation is before the time point of initiating the administration of the therapeutic agent. In the above requirements 2 to 4, the expression "stimulation is performed within n hours after administration of the therapeutic agent" means that the time point of initiating the stimulation is before the time point at which n hours have passed from the time point of initiating the administration of the therapeutic agent.

In the above requirement 2, from the viewpoint of greater likelihood of exhibiting the effect of the present invention, stimulation is preferably performed between before and 10 hours after administration of the therapeutic agent. In such a case, from the viewpoint of particularly greater likelihood of exhibiting the effect of the present invention, stimulation is preferably performed within 3 hours after administration of the therapeutic agent, following the nasal administration of the culture supernatant in the present invention.

In the above requirement 2, from the viewpoint of greater likelihood of exhibiting the effect of the present invention, stimulation is preferably performed at a time point preferably between immediately after and 1 hour after nasal administration, more preferably between 5 minutes after and 1 hour after nasal administration, and most preferably between 30 minutes after and 1 hour after nasal administration.

In the above requirement 2, the reason why stimulation is preferably performed at a time point between immediately after and 1 hour after nasal administration is as follows. The administered cultured supernatant in the present invention usually has an increased blood concentration and an increased cerebrospinal fluid concentration immediately after administration. Then, the culture supernatant concentration sharply drops within about 24 hours in blood and about 12 hours in the cerebrospinal fluid, and drops to an undetectable level in the affected area (the brain etc.) 24 hours after administration. In the case of nasal administration, examples of the path, through which the culture supernatant is transferred into a cerebrospinal fluid, include not only the one mediated by blood, but also an early direct transfer path, through which the administered culture supernatant passes through the nasal epithelial cells, reaches the cerebrospinal fluid around the olfactory nerve bundle, and thus is transferred to the cerebrospinal fluid in the subarachnoid space. Through such a path, the cerebrospinal fluid concentration of the culture supernatant increases to several tens of times or more the blood concentration, for example, within about 15 to 30 minutes after administration. Since there is no substance transfer barrier between cerebrospinal fluids and brain tissues, the amount of the drug (culture supernatant) in the cerebrospinal fluid can correspond to the amount of the drug (culture supernatant) in the extracellular fluid of the brain tissue. Therefore, since a time point between immediately after and 1 hour after nasal administration is the timing at which the amount of drug in the extracellular fluid of the brain tissue is the highest, the effect of the present invention can be exhibited more efficiently by applying stimulation at this time point.

In another form of the above requirement 2, from the viewpoint of easily exhibiting the effect of the present invention, the culture supernatant in the present invention is nasally administered before sleep (for example, 0 to 3 hours before sleep) and then stimulation may be performed after sleep (for example, immediately after awakening to 5 hours after awakening). It is considered that sleep results in increases in the blood concentration and the cerebrospinal fluid concentration of the culture supernatant (supernatant fluid). In addition, sleep stimulation tends to cause neural circuit resynthesis. From the above, the effect of the present invention can be more efficiently exhibited by using sleep stimulation in combination after nasal administration.

In the above requirement 2, regardless of the initiation of stimulation, the decubitus position may be maintained for at least about 15 to 30 minutes after administration in order to make the culture supernatant to remain as easily as possible in the nasal cavity after nasal administration. In addition, a patient may shift to a sleep state for a short time (for example, within 1 hour) immediately after administration.

In the above requirement 2, a particularly preferable form is as follows. Immediately after nasal administration of the culture supernatant in the present invention, selected stimulation (preferably magnetic stimulation in the decubitus position) is applied for 1 to 20 minutes, for example. During stimulation, a patient may shift to a sleep state. After stimulation, another selected stimulation (preferably, motor stimulation) may be further applied. When a patient is shifting to a sleep state during stimulation, nasal administration is performed before falling asleep, and is preferable if the patient falls asleep as soon as possible (for example, within 1 hour after administration). In the above form, nasal administration may be performed once or twice or more, and may be performed, for example, before the shift to a sleep state or immediately before the stimulation.

In the above requirement 3, from the viewpoint of greater likelihood of exhibiting the effect of the present invention, stimulation is preferably performed between before and 1 hour after administration of the therapeutic agent.

In the above requirement 4, from the viewpoint of greater likelihood of exhibiting the effect of the present invention, stimulation is performed preferably between before and 10 hours after, more preferably between before and 4 hours after, and further preferably between before and 3 hours after administration of the therapeutic agent.

The term "stimulation" used herein refers to stimulation that causes a physiological change (at least one, preferably two or more of an electrical change, a change in blood flow rate, a change in metabolic rate, etc.) in the site that has been stimulated. The intensity of stimulation to be applied in the present invention can be appropriately adjusted depending on the effect to be obtained and the situation (age, body weight, degree of symptom, etc.) of a patient to be subjected to administration.

The expression "stimulation of a nerve of a patient" used herein means that stimulation applied to the whole or a part of the body of a patient causes the nerve to produce any reaction. At this time, a form in which stimulation is applied to any tissue and the like adjacent to the nerve is not excluded. Stimulation to be applied to a patient may be performed by stimulating only one site or multiple sites in the nerve.

The stimulation of the present invention may be applied at one or more time points of before, during, and after administration of the therapeutic agent of the present invention.

The kind of stimulation to be applied to a patient is not particularly limited, as long as it can realize stimulation of a nerve. From the viewpoint of easily enhancing the therapeutic effect according to the present invention, stimulation is preferably one or more kinds of stimulation selected from the group consisting of motor stimulation, sensory stimulation, electrical stimulation, magnetic stimulation, verbal stimulation, and higher brain function stimulation. One or more of these kinds of stimulation may be applied simultaneously by one means for applying stimulation. For example, with the use of a voluntary movement-assisted electric stimulator, motor stimulation, sensory stimulation (somatosensory stimulation), and electrical stimulation can be simultaneously applied to a patient. When a robot assisted training device (for example, "Robot Suit HAL" (trademark)) is used in combination, motor stimulation and sensory stimulation can be simultaneously applied to a patient.

[Motor stimulation] The term "motor stimulation" used herein refers to motor stimulation targeting an affected area. Here, motor stimulation accompanied by whole-body exercise (e.g., an exercise using a treadmill or the like) is not excluded as an example of the motor stimulation targeting an affected area. Examples of the forms of the motor stimulation include, in order to increase the amount of stimulation to be applied to a target nerve tract, a form using neuromuscular facilitation (PNF method, Brunnstrom method, Bobath method, etc.) in combination, a form that is intensive repetitive motor stimulation such as, Kawahira method (Repetitive Facilitative Exercise) and Arm Basis training, a form of forcefully performing motor stimulation such as Constrain-Induced Movement Therapy (CI therapy), and a form of using not only motor stimulation, but also sensory stimulation, electrical stimulation, and magnetic stimulation in combination as stimulation to be applied. Further, the use of a robot-assisted training device (for example, "Robot Suit HAL" (trademark)) makes it possible to simultaneously apply repeated motor stimulation and sensory stimulation to a patient.

A preferable example of stimulation to be applied to a patient with dysphagia is a combined use of arbitrary motor stimulation and swallowing training. A preferable example of stimulation to be applied to a patient with dysarthria is a combined use of arbitrary motor stimulation and articulation training.

Motor stimulation is a kind of stimulation to be applied to the motor nerve pathway. The motor nerve pathway is a pathway that transmits motor information from upper motor neurons (starting from the cerebral cortical primary motor area and the brain stem) to lower motor neurons. Examples of this pathway include the lateral corticospinal tract, the rubrospinal tract, the reticular spinal tract, the vestibular spinal tract, the tectospinal tract, and the corticospinal tract. Further, the motor nerve pathway forms synapses with lower motor neurons, and the axons extend as a peripheral nerve to form synapses with the extrapyramidal muscle fiber, so as to contract the target muscle and cause movement. The primary motor area is regulated by the premotor area, the supplementary motor area, the zonal cortex motor area, the thorax, the primary somatosensory area, the superior parietal lobule, etc., and the motor nerve pathway and the sensory nerve pathway constantly function while regulating to each other.

[Sensory stimulation] The term "sensory stimulation" used herein refers to stimulation to be applied to any one of the sensations (visual sense, auditory sense, tactile sense, etc.) related to nerve disorders. From the viewpoint of easily exhibiting the effect of the present invention, somatosensory stimulation, auditory stimulation, and visual stimulation are preferable as the sensory stimulation in the present invention.

The term "somatosensory stimulation" used herein refers to a general term for skin sensation, deep sensation, and visceral sensation. Specific examples thereof include sensations (pain sensation, temperature (low temperature to high temperature) sensation, tactile pressure sensation, etc.) obtained from skin, mucous membranes, joints, muscles, tendons and the like.

A means for applying somatosensory stimulation to a patient is not particularly limited, and examples thereof include tactile pressure, acupuncture and moxibustion, heat, weight, and vibration.

Examples of the tactile pressure include rehabilitation (for example, massage performed while visually confirming the damaged part) for a part with a nerve disorder (hand, foot, etc.).

Examples of the acupuncture and moxibustion include methods using needles and moxibustion (burning moxa).

Examples of the heat include methods using moxibustion (burning moxa), heat packs, and water treatment.

Examples of the weight include methods using a weight band for performing a light resistance exercise, which is used for rehabilitation.

Examples of the vibration include methods using vibration.

The term "auditory stimulation" used herein refers to stimulation to be applied using sound. The sound is not particularly limited, and examples thereof include voices of humans and the like, and arbitrary music (certain rhythmic rhythm, etc.).

A means for applying auditory stimulation to a patient is not particularly limited, but may be Rhythmic Auditory Stimulation (RAS) or the like.

The term "visual stimulation" used herein refers to stimulation to be applied using visual information. The visual information is not particularly limited, and examples thereof include arbitrary information (characters, images, videos, etc.) existing in the space.

A means for applying visual stimulation to a patient is not particularly limited, and examples thereof include functional training (visual search task, visual scanning training, etc.), activities surrounding day-to-day living (eating, changing clothes, excretion, dressing, bathing, reading, painting, etc.), and prism adaptation.

Sensory stimulation is usually stimulation to be applied to somatic sensations (sensations obtained from skin, mucous membranes, joints, muscles, tendons, etc.). Somatic sensation is roughly divided into four modalities (pain sensation, temperature sense, tactile pressure sensation, deep (unique) perception), and sensory receptors, nerve fibers, conduction pathways, etc. specialized for each reception are used. The sensory nerve pathway through which somatic sensations reach the cerebral cortex has been clarified. For example, the following pathways are known. Deep sensation and fine tactile pressure sensation: Passes through the dorsal column-medial ciliary pathway system (receptor→primary neurons (enters the spinal cord, ascends the ipsilateral dorsal column, and terminates at the ipsilateral medullary dorsal column nuclei)→secondary neurons (crosses and ascends the contralateral medial lemniscus and terminates at the contralateral thalamic VPL)→reaches tertiary neurons (contralateral cerebral cortical somatosensory area)). Thermal nociception course tactile pressure sensation: Passes through the spinothalamic tract (receptor→primary neurons (enters the spinal cord and terminates at the posterior horn of the spinal cord)→secondary neurons (crosses and ascends the contralateral anterior cord, ascends the contralateral spinothalamic tract, and terminates at the contralateral thalamic VPL)→reaches tertiary neurons (contralateral cerebral cortex somatosensory area)).

[Electrical stimulation] The term "electrical stimulation" used herein refers to stimulation to be electrically applied using an electric current. An example thereof is stimulation that excites the neural circuits with electricity (low frequency, medium frequency, high frequency, interference wave, etc.) from an electrode attached to an affected area.

A means for applying electrical stimulation to a patient is not particularly limited, and a method using an integrated volitional control electrical stimulator (IVES) etc. and a method conventionally known as an electric current stimulation therapy (Transcutaneous Electrical Nerve Stimulation (TENS) method, Functional Electrical Stimulation (FES) method, Therapeutic Electrical Stimulation (TES) method, transcranial Direct Current Stimulation (tDCS), Deep Brain Stimulation (DBS) method, etc.) may be used.

Electrical stimulation usually repeatedly excites the neural circuits with low frequency, medium frequency, high frequency, interference waves, or the like via electrodes attached to the paralyzed limbs. By exciting the neural circuits by electrical stimulation, it is possible to raise the pain threshold as described by the gate control theory, or lower the motor threshold to make the paralyzed limbs easier to move.

[Magnetic stimulation] The term "magnetic stimulation" used herein refers to stimulation to be applied magnetically using static magnet or electromagnet.

A means for applying magnetic stimulation to a patient is not particularly limited, and a method conventionally known as magnetic stimulation (for example, Transcranial Magnetic Stimulation (TMS), Transcranial Direct Current Stimulation (tDCS) that involves stimulating with weak electric current, and Deep Brain Stimulation (DBS) that involves placing an electrode deep in the brain, and continuously electrically stimulating the nervous system to control the functions for treatment) may be used. In the case of TMS, classical rTMS techniques such as low-frequency rTMS (1 Hz or less) that acts on inhibitory and high-frequency rTMS (5 Hz or more) that acts on excitability are typical. "Theta burst stimulation (TBS)" that involves applying the burst stimulation consisting of 3 consecutive stimulations of 50 Hz at a frequency of 5 Hz may be used. Intermittent TBS (iTBS) involves performing pulse stimulation, by which theta burst stimulation (3 consecutive stimulations of 50 Hz at 5 Hz) is performed for 2 seconds, followed by 8 seconds of resting, thereby enhancing the excitability of the motor area. Further, continuous TBS (cTBS) involves continuously performing theta burst stimulation (3 consecutive stimulations of 50 Hz at 5 Hz), so as to inhibit the excitability in the motor area. Specifically, TBS exhibits an inhibitory effect when it is continuously performed, and exhibits an excitatory effect when it is performed intermittently. TBS is characterized in that TBS can be performed with a weaker stimulation intensity than that of low-frequency or high-frequency rTMS, and has a longer duration of action than that of the same.

[Verbal stimulation] The term "verbal stimulation" used herein refers to stimulation to be applied by communication through language.

A means for applying verbal stimulation to a patient is not particularly limited, and an example thereof is encouraging a patient to do something such as reading, writing, drawing, listening, speaking, reciting, calculating or the like.

Verbal stimulation is usually stimulation to be applied to language-related brain areas (Broca's area, Wernicke's area, left angular gyrus (Brodmann area 39), left supramarginal gyrus (Brodmann area 40), cerebellum, thalamus, basal ganglia, etc.).

[Higher brain function stimulation] The term "higher brain function" used herein refers to a general term for mental (psychological) functions including cognitive processes (perception, memory, learning, thinking, judgment, etc.) and emotions (feelings) of actions. The term "higher brain function stimulation" used herein refers to memory training, attention training, executive function training, and social behavior training.

A means for applying higher brain function stimulation to a patient is not particularly limited, and an example thereof is encouraging a patient to perform memory training, attention training, executive function training, social behavior training, or the like.

Higher brain function stimulation is, when a target of stimulation is a frontal lobe function or the like, usually stimulation to be applied to any one of pyramidal hierarchy ranging from the lowest layer, awakening→inhibition initiation→attention and concentration→information processing→memory→executive function logical thinking ("Comprehensive Rehabilitation May 2006 Issue (Igaku-Shoin Ltd.)").

[Other kinds of stimulation] The term "stimulation" in the present invention includes any stimulation that can bring about a physiological change in the patient, in addition to the above examples. For example, when stimulation is a form that is applied between before and 6 hours after administration of the therapeutic agent, the stimulation may be whole-body exercise or the like.

[Confirmation and evaluation of stimulation] In the present invention, whether or not stimulation is applied to a patient and its intensity are specified by the presence or absence and degree of physiological changes in the patient.

Examples of physiological changes serving as indicators of stimulation include electrical changes, changes in blood flow rate, and changes in metabolic rate (metabolic rate of oxygen or the like). Usually, the stronger the applied stimulation, the greater the amounts of changes in these physiological changes. For example, the stronger the stimulation applied, the higher the blood flow rate and metabolic rate in the brain.

Electrical changes are specified by non-invasive brain function measurement methods such as scalp electroencephalography (EEG) and magnetoencephalography (MEG).

Changes in blood flow rate are specified by non-invasive brain function measurement methods such as functional MRI (functional Magnetic Resonance Imaging) and SPECT (Single Photon Emission CT) that are performed with respect to changes in cerebral blood flow rate, for example.

Changes in cerebral blood flow and oxygen metabolic rate are specified by optical topography, PET (Positron Emission Tomography) examination, and the like.

[Timing of applying stimulation] Stimulation may be applied once or multiple times at any time point during a period specified in the present invention. However, stimulation that is applied at a time point even after a period specified in the present invention is not excluded.

When stimulation is performed before administration of the therapeutic agent, the timing of applying the stimulation can be appropriately set depending on the kind of stimulation, the patient's condition, and the like.

The time required for the rate of blood flow to an affected area (e.g., nerve injury site) and metabolic rate to increase after stimulation, and the time for maintaining such increases in blood flow rate and metabolic rate may differ depending on the kind of stimulation. Therefore, it is preferable to adjust the timing of administering the therapeutic agent, so as to overlap with the timing of higher blood flow rate and higher metabolic rate in the affected area. Specifically, when the stimulation is sensory stimulation or verbal stimulation, the time required for the rate of blood flow to an affected area to increase and the metabolic rate to increase after stimulation tends to be longer than those of a case where the stimulation is electrical stimulation or magnetic stimulation. Therefore, when the stimulation is sensory stimulation or verbal stimulation, it is preferable to set a longer period from the stimulation to the administration of the therapeutic agent, or a shorter period from the administration of the therapeutic agent to the stimulation. On the other hand, when the stimulation is electrical stimulation or magnetic stimulation, it is preferable to set the time from the stimulation to the administration of the therapeutic agent short, and it is possible to set the time from the administration of the therapeutic agent to the stimulation long.

[Site to be stimulated When stimulation is preferentially applied to one or more sites selected from the group consisting of a nerve injury site, an area surrounding the nerve injury site, and a site compensating for the function of the nerve injury site, stimulating a site other than these sites is not excluded.

The expression "preferentially applied to (a predetermined site)" used herein means that when stimulation is initiated, stimulation is initially applied for to one or more sites selected from the group consisting of a nerve injury site, an area surrounding the nerve injury site, and sites compensating for the function of the nerve injury site.

The term "nerve injury site" used herein refers to the site itself where a nerve injury (atrophy, nerve blockage, transection, rupture, defect, brain injury, spinal cord injury, etc.) has occurred. In general, a nerve injury site causes a nerve disorder(s).

The term "an area surrounding the nerve injury site" used herein refers to a site that is not a nerve injury site itself, but corresponds to an area surrounding the nerve injury site (for example, a site surrounding the nerve injury site or a site close to the nerve injury site).

The term "a site compensating for the function of the nerve injury site" used herein refers to sites serving to compensate for the function of the nerve injury site (for example, when the primary motor area is damaged, the right parietal lobe of the peripheral part on the affected side and the primary motor area, premotor area, supplementary motor area, etc. on the healthy side).

Examples of the site of a patient, which is to be stimulated, include the head (brain, etc.), face, eyes, ears, mouth, upper limbs, lower limbs, trunk, articulation organs, swallowing organs, and the like.

Sites to be stimulated and methods for applying stimulation are illustrated below for each type of stimulation.

[Examples of applying motor stimulation] In the case of nerve damage to the right primary motor area (finger control part), "the nerve injury site" is the right primary motor area (finger control part). In the case of nerve damage to the right primary motor area (finger control part), "the area surrounding the nerve injury site" is the right primary motor area (other than finger control part) to the premotor area, a supplementary motor area, the right primary sensory area, or the like, which has escaped damage. In the case of nerve damage to the right primary motor area (finger control part), "the site compensating for the function of the nerve injury site" is the right parietal lobe, the left primary motor area to the premotor area, a supplementary motor area, or the like.

In the case of nerve damage to the right primary motor area (finger control part), trying to move paralyzed left fingers can preferentially stimulate the nerve injury site. In the case of nerve damage to the right primary motor area (finger control part), trying to move sites close to paralyzed left fingers (left fingers, left wrist, etc., having escaped damage) can preferentially stimulate the areas surrounding the nerve injury site. In the case of nerve damage to the right primary motor area (finger control part), encouraging a patient to achieve various challenges such as using paralyzed left fingers and encouraging a patient to roughly move paralyzed left fingers can preferentially stimulate the site(s) compensating for the function of the nerve injury site.

[Examples of applying sensory stimulation] In the case of nerve damage to the right primary sensory area (tertiary neurons), "the nerve injury site" is the right primary sensory area. In the case of nerve damage to the right primary sensory area (tertiary neurons), "the area surrounding the nerve injury site" is the right primary sensory area to the right primary motor area, or the like, which has escaped damage. In the case of nerve damage to the right primary sensory area (tertiary neurons), "the site compensating for the function of the nerve injury site" is the left primary sensory area, the secondary somatosensory area communicating with the primary sensory area, the parietal lobe association area, motor area, visual area, or the like.

In the case of nerve damage to the right primary sensory area (tertiary neurons), applying sensory stimulation to an affected area with a sensory disorder can preferentially stimulate the nerve injury site. In the case of nerve damage to the right primary sensory area (tertiary neurons), stimulating a site close to a site with sensory disorder can preferentially stimulate the area surrounding the nerve injury site. In the case of nerve damage to the right primary sensory area (tertiary neurons), instructing a patient to make visual confirmation, when sensory stimulation is applied to a site with a sensory disorder or the periphery thereof, and applying sensory stimulation to the same degree to both the healthy side and the affected side simultaneously can preferentially stimulate a site(s) compensating for the function of the nerve injury site.

[Examples of applying electrical stimulation] In the case of nerve damage to the right second finger, "the nerve injury site" is the right second finger. In the case of nerve damage to the right second finger, "the area surrounding the nerve injury site" is the right first, third, fourth, and fifth fingers, or the like, which has escaped nerve damage. In the case of nerve damage to the right second finger, "the site compensating for the function of the nerve injury site" is the right wrist, forearm, upper arm, shoulder, or the like.

In the case of nerve damage to the right second finger, applying electrical stimulation to the right second finger that is the nerve injury site can preferentially stimulate the nerve injury site. In the case of nerve damage to the right second finger, applying electrical stimulation to the right first, third, fourth, or fifth finger close to the right second finger with a nerve disorder can preferentially stimulate the area surrounding the nerve injury site. In the case of nerve damage to the right second finger, applying electrical stimulation to the right wrist, forearm, upper arm, or shoulder can preferentially stimulate the site compensating for the function of the nerve injury site.

[Examples of applying magnetic stimulation] In the case of nerve damage to the right primary motor area (finger control part), "the nerve injury site" is the right primary motor area (finger control part). In the case of nerve damage to the right primary motor area (finger control part), "the area surrounding the nerve injury site" is the right primary motor area (other than finger control part) to the premotor area, a supplementary motor area, the right primary sensory area, or the like, which has escaped damage. In the case of nerve damage to the right primary motor area (finger control part), "the site compensating for the function of the nerve injury site" is the right parietal lobe, the left primary motor area to the premotor area, a supplementary motor area, or the like.

In the case of nerve damage to the right primary motor area (finger control part), applying excitatory magnetic stimulation (high frequency rTMS <5 Hz or more> or intermittent TBS, etc.) to the right primary motor area (finger control part) can preferentially stimulate the nerve injury site. In the case of nerve damage to the right primary motor area (finger control part), applying excitatory magnetic stimulation to sites close to the nerve injury site including the right primary motor area (other than finger control part) to the premotor area, a supplementary motor area, and the right primary sensory area can preferentially stimulate the areas surrounding the nerve injury site. In the case of nerve damage to the right primary motor area (finger control part), applying excitatory magnetic stimulation to the right parietal lobe can preferentially stimulate the site compensating for the function of the nerve injury site. Further, applying inhibitory magnetic stimulation (low frequency rTMS <1 Hz or less> or continuous TBS) to the left primary motor area lowers the inhibition (interhemispheric inhibition) of the activity of the area ranging from the left cerebrum to the right cerebrum, and as a result, releases the nerve injury site (right primary motor area <finger control part>), a peripheral part (right primary motor area <other than finger control part> to the premotor area, a supplementary motor area, the right primary sensory area), and a compensatory part (right parietal lobe) from inhibition, so as to be able to increase the blood flow and excitability.

[Examples of applying verbal stimulation] In the case of nerve damage to Wernicke's area, "the nerve injury site" is Wernicke's area. In the case of nerve damage to Wernicke's area, "the area surrounding the nerve injury site" is the language circuit or the like including Wernicke's area, Broca's area, and the conducting pathway (the fasciculus arcuatus) connecting the two, which has escaped damage. In the case of nerve damage to Wernicke's area, "the site compensating for the function of the nerve injury site" is the left angular gyrus (Brodmann area 39), the left supramarginal gyrus (Brodmann area 40), the cerebellum, the thalamus, the basal ganglia, or the like.

In the case of nerve damage to Wernicke's area, applying sensory verbal stimulation can preferentially stimulate the nerve injury site. In the case of nerve damage to Wernicke's area, instructing a patient to read back and applying motor verbal stimulation can preferentially stimulate the area surrounding the nerve injury site. In the case of nerve damage to Wernicke's area, providing challenges in terms of vocal sounds, words, grammar, comprehension, calculation, and the like can preferentially stimulate the site compensating for the function of the nerve injury site.

[Examples of applying higher brain function stimulation] In the case of impaired executive functions caused by nerve damage, "the nerve injury site" is a brain site controlling the executive function. In the case of impaired executive functions caused by nerve damage, "the area surrounding the nerve injury site" is a brain site controlling memory and information processing in a layer below the layer of the executive function. In the case of impaired executive functions caused by nerve damage, "the site compensating for the function of the nerve injury site" is a brain site controlling attention, concentration, inhibition, spontaneity, alertness, etc., which are in a layer further below the layer of memory and information processing.

In the case of impaired executive function caused by nerve damage, training for executive functions can preferentially stimulate the nerve injury site. In the case of impaired executive functions caused by nerve damage, training for memory and information processing in a layer below the layer of executive functions can preferentially stimulate the area surrounding the nerve injury site. In the case of impaired executive functions caused by nerve damage, training for attention, concentration, inhibition, spontaneity, and alertness, which are in a layer further below the layer of memory and information processing, can preferentially stimulate the site(s) compensating for the function of the nerve injury site.

EXAMPLES

Hereinafter, the present invention will be described in more detail by way of examples, but the present invention is not limited to these examples.

<Preparing culture supernatant of mesenchymal stem cells> Mesenchymal stem cells derived from each tissue were cultured by the following method, and the culture supernatant was collected.

All cells were cultured as follows at a temperature of 37° C. and a $CO_2$ concentration of 5% in an incubator for 3 weeks.

(1) Culturing Bone Marrow-Derived Mesenchymal Stem Cells

With the use of "KBM ADSC-2" (Kohjin Bio Co., Ltd.), bone marrow-derived mesenchymal stem cells were separated from a human bone marrow tissue, and then the thus obtained mesenchymal stem cells were cultured. Cells were removed from the obtained culture using a 0.1 μm to 0.22 μm PVDF filter, so that a culture supernatant of bone marrow-derived mesenchymal stem cells (hereinafter, may also be referred to as "culture supernatant-1") was obtained. The thus obtained culture supernatant had a soluble solid content of 2 mg/ml.

(2) Culturing Adipose-Derived Mesenchymal Stem Cells

In the same manner as in the above "(1) Culturing bone marrow-derived mesenchymal stem cells", a culture supernatant of adipose-derived mesenchymal stem cells was obtained using mesenchymal stem cells obtained from a human adipose tissue. Cells were removed from the obtained culture using a 0.1 μm to 0.22 μm PVDF filter, a culture supernatant of adipose-derived mesenchymal stem cells (hereinafter, may also be referred to as "culture supernatant-2") was obtained. The thus obtained culture supernatant had a soluble solid content of 2 mg/ml.

(3) Culturing Dental Pulp-Derived Mesenchymal Stem Cells

In the same manner as in the above "(1) Culturing bone marrow-derived mesenchymal stem cells", a culture supernatant of dental pulp-derived mesenchymal stem cells was obtained using mesenchymal stem cells obtained from a human dental pulp tissue. Cells were removed from the obtained culture using a 0.1 μm to 0.22 μm PVDF filter, so that a culture supernatant of dental pulp-derived mesenchymal stem cells (hereinafter, may also be referred to as "culture supernatant-3") was obtained. The thus obtained culture supernatant had a soluble solid content of 2 mg/ml.

(4) Culturing Umbilical Cord-Derived Mesenchymal Stem Cells

In the same manner as in the above "(1) Culturing bone marrow-derived mesenchymal stem cells", a culture supernatant of umbilical cord-derived mesenchymal stem cells was obtained using mesenchymal stem cells obtained from a human umbilical cord tissue. Cells were removed from the obtained culture using a 0.1 μm to 0.22 μm PVDF filter, so that a culture supernatant of umbilical cord-derived mesenchymal stem cells (hereinafter, may also be referred to as "culture supernatant-4") was obtained. The thus obtained culture supernatant had a soluble solid content of 2 mg/ml.

<Treatment for patient> The above-prepared culture supernatants were administered to patients with the following symptoms of nerve disorders. Administration was performed for each patient by either one type of nasal administration, intravenous administration, and subcutaneous administration. Concurrently, stimulation (either one of motor stimulation, sensory stimulation, electrical stimulation, magnetic stimulation, verbal stimulation, and higher brain function stimulation) was applied.

(Administering culture supernatant) The culture supernatants were each administered to each patient by each of the following methods.

The timing of administering each culture supernatant was varied for each individual patient depending on the administration method. Details of the timing of administering each culture supernatant are as shown in the leftmost column of each of Tables 1 to 15. Note that the term "n hours before administration" means that the time point of initiating the stimulation was n hours before the time point of initiating the administration of the culture supernatant. The term "immediately after administration" means that the time point of initiating the stimulation was immediately after administration of the culture supernatant (any one of time points within 15 minutes after administration of the culture supernatant). The term "n hour(s) after administration" means that the time point of initiating the stimulation was n hours after the time point of initiating the administration of the culture supernatant.

The culture supernatant type (any one of culture supernatant-1 to 5) administered is as described in the columns of "culture supernatant" in each of Tables 1 to 15.

(1) Nasal Administration

To each patient, 1 ml of a culture supernatant was administered intranasally to both sides using a general nasal drop container. Administration was performed every day for 14 weeks. Regarding nasal administration performed immediately after the initiation of administration, nasal administration performed 30 minutes after administration, nasal administration performed 3 hours after administration, nasal administration performed 10 hours after administration, and nasal administration performed 20 hours after administration, each nasal administration was varied in two cases, the one in which a patient was instructed to get one hour of sleep immediately after administration, and, the other one in which a patient was instructed to get no sleep immediately after administration.

(2) Intravenous Administration

To each patient, 5 ml of a culture supernatant was administered by drip infusion for 1 hour. Administration was performed every 7 days for 4 weeks.

(3) Subcutaneous Administration

To each patient, 2 ml of a culture supernatant was subcutaneously administered to the side of upper arm extensor. Administration was performed every 7 days for 4 weeks.

(Stimulation) Details about stimulation applied to each patient are as described below.

[Motor stimulation] For a group of patients in their 40 s and 50 s who had cerebral hemorrhages, Repetitive Facilitative Exercise was performed as motor stimulation. In this example, the sites to be stimulated were set at the nerve injury sites (left finger, left foot to lower leg), the areas surrounding the nerve injury sites (left wrist joint to forearm, left knee joint to thigh), and sites compensating for the function of the nerve injury sites (left elbow joint to shoulder joint, left hip joint). The time for applying stimulation per session was set to 30 minutes for each site. Further, a group of patients in their 40 s and 50 s with similar symptoms was instructed to perform whole-body exercise (30 minutes per treadmill workout), and then a culture supernatant was administered in the same manner as described above.

[Sensory stimulation] To patients with sensory disorder among a group of patients in their 40 s and 50 s who had cerebral hemorrhages, sensory stimulation was applied to their upper and lower extremities. Specifically, auditory stimulation (speaking to them) was applied to these patients, while applying cooling stimulation with an ice bag to paralyzed upper and lower extremities, and an instruction is given to visually confirm the positions of the upper and lower extremities. In this example, the sites to be stimulated were set at the nerve injury sites (left finger, left foot to lower leg), the areas surrounding the nerve injury sites (left wrist joint to forearm, left knee joint to thigh), and sites compensating for the function of the nerve injury sites (left elbow joint to shoulder joint, left hip joint). The time for applying stimulation per session was set to 30 minutes for each site. The above sensory stimulation was applied to the upper and lower extremities on the affected side. Further, to the upper and lower extremities on the healthy side of a group of patients in their 40 s and 50 s with similar symptoms, sensory stimulation (30 minutes per session) was applied, and then a culture supernatant was administered in the same manner as described above.

[Electrical stimulation] To a group of patients in their 40 s and 50 s who had cerebral hemorrhages, electrical stimulation was applied to their paralyzed upper and lower extremities. Specifically, low-frequency stimulation was applied to their paralyzed hands and feet via electrodes attached to the hands and feet. In this example, the sites to be stimulated were set at the nerve injury sites (left finger, left foot to lower leg), the areas surrounding the nerve injury sites (left wrist joint to forearm, left knee joint to thigh), and sites compensating for the function of the nerve injury sites (left elbow joint to shoulder joint, left hip joint). The time for applying stimulation per session was set to 20 minutes for each site. The above electrical stimulation was applied to the upper and lower extremities on the affected side. Further, to the upper and lower extremities on the healthy side of a group of patients in their 40 s and 50 s with similar symptoms, electrical stimulation (20 minutes per session) was applied, and then a culture supernatant was administered in the same manner as described above.

[Magnetic stimulation] Transcranial magnetic stimulation was applied to the heads of a group of patients in their 40 s and 50 s who had cerebral hemorrhages using a TMS device (CR Technology Co., Ltd.). Specifically, intermittent TBS (iTBS; 1 burst 50 Hz, 3 stimuli) consisting of a total of 2,000 pulses (2 seconds on and 8 seconds off) was applied at 80% of motor threshold and 5 Hz (time intervals of 200 ms). In this example, the sites to be stimulated were set at the nerve injury sites (the finger control part in the primary motor area on the affected side), the areas surrounding the nerve injury sites (other than finger control part in the primary motor area on the affected side), the sites compensating for the function of the nerve injury sites (right parietal lobe). The time for applying stimulation per session with 2,000 pulses was set to about 11 minutes for each site. The above magnetic stimulation was applied to the head on the affected side. Further, to a group of patients in their 40 s and 50 s with similar symptoms, placebo magnetic stimulation (2,000 pulses per session, about 11 minutes) generating only sound was applied to an affected area of the head, and then each culture supernatant was administered in the same manner as described above. Note that placebo magnetic stimulation to be applied to an affected area of the head applies actually no magnetic stimulation to patients.

[Verbal stimulation] To patients confirmed to have aphasia from among a group of patients in their 70 s and 80 s who had cerebral hemorrhages, verbal stimulation was applied.

Verbal stimulation was applied using challenges in communication (reading, writing, hearing, speaking, read back, calculation). The time for applying stimulation was set to 60 minutes.

[Higher brain function stimulation] To patients confirmed to have higher brain dysfunction (inattention) from among a group of patients in their 70 s and 80 s who had cerebral hemorrhages, higher brain function stimulation was applied. As higher brain function stimulation, Attention Process Training was performed as attention training. The time for applying stimulation was set to 60 minutes.

[Reference test] As a reference, patients confirmed to have aphasia from among a group of patients in their 70 s and 80 s who had cerebral hemorrhages were instructed to listen to the radio or view the TV for 1 hour passively.

<Therapeutic effect on nerve disorders> Each treatment was performed for patients, the therapeutic effect on each symptom was evaluated using the following indicators, and then the evaluation results were classified based on the following criteria. The results are shown in Table 1.

Note that the expression "the longest test time after administration of the culture supernatant" in each evaluation criterion refers to the time point at which the longest test time has passed after administration performed according to each method. For example, in the case of nasal administration, "the longest test time after administration of the culture supernatant" refers to "20 hours after administration".

(Evaluation) Paralysis sensory disorder: SIAS (Stroke Impairment Assessment), FMA (Fugl-Meyer Assessment)

Cerebral infarction: NIHSS (National Institutes of Health Stroke Scale)

Aphasia: Standard Language Test of Aphasia (SLTA)

Higher brain function: MMSE (Mini-Mental State Examination)

(Evaluation Criteria-Motor Stimulation)

A (Very good): A marked therapeutic effect was observed compared with the result of whole-body exercise (the longest test time after administration of the culture supernatant).

B (Good): A therapeutic effect was observed compared with the result of whole-body exercise (the longest test time after administration of the culture supernatant).

C (Fair): Some therapeutic effect was observed compared with the result of whole-body exercise (the longest test time after administration of the culture supernatant).

(Evaluation Criteria-Sensory Stimulation, Electrical Stimulation)

A (Very good): A marked therapeutic effect was observed compared with the result of stimulation applied to the healthy side (the longest test time after administration of the culture supernatant).

B (Good): A therapeutic effect was observed compared with the result of stimulation applied to the healthy side (the longest test time after administration of the culture supernatant).

C (Fair): Some therapeutic effect was observed compared with the result of stimulation applied to the healthy side (the longest test time after administration of the culture supernatant).

(Evaluation Criteria-Magnetic Stimulation)

A (Very good): A marked therapeutic effect was observed compared with the result of placebo magnetic stimulation applied to the affected side (the longest test time after administration of the culture supernatant).

B (Good): A therapeutic effect was observed compared with the result of placebo magnetic stimulation applied to the affected side (the longest test time after administration of the culture supernatant).

C (Fair): Some therapeutic effect was observed compared with the result of placebo magnetic stimulation applied to the affected side (the longest test time after administration of the culture supernatant).

(Evaluation Criteria-Verbal Stimulation, Higher Brain Function Stimulation, Reference Test)

A (Very good): A significant therapeutic effect was observed compared with that before the administration of the culture supernatant and stimulation.

B (Good): A therapeutic effect was observed compared with that before the administration of the culture supernatant and stimulation.

C (Fair): Some therapeutic effect was observed compared with that before the administration of the culture supernatant and stimulation.

D (Poor): No change was observed compared with that before the administration of the culture supernatant and stimulation.

TABLE 1

| | Motor stimulation | | | | | | | | | | | | | | | |
| Nasal | Nerve injury site | | | | Area surrounding nerve injury site | | | | Site compensating for the function of nerve injury site | | | | Whole-body exercise | | | |
| | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
| --- | --- | --- | --- | --- | --- | --- | --- | --- | --- | --- | --- | --- | --- | --- | --- | --- |
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | B | B | B | B | B | B | B | B | B | B | B | B | C | C | C | C |
| 30 minutes after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | B | B | B | B | B | B | B | B | B | B | B | B | C | C | C | C |
| 20 hours after administration | C | C | C | C | C | C | C | C | C | C | C | C | — | — | — | — |

TABLE 2

| | Sensory stimulation to the affected side | | | | | | | | | | | | | | | |
| Nasal | Nerve injury site | | | | Area surrounding nerve injury site | | | | Site compensating for the function of nerve injury site | | | | Whole-body exercise | | | |
| | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
| --- | --- | --- | --- | --- | --- | --- | --- | --- | --- | --- | --- | --- | --- | --- | --- | --- |
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | B | B | B | B | B | B | B | B | B | B | B | B | C | C | C | C |
| 30 minutes after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | B | B | B | B | B | B | B | B | B | B | B | B | C | C | C | C |
| 20 hours after administration | C | C | C | C | C | C | C | C | C | C | C | C | — | — | — | — |

TABLE 3

| Nasal administration | Electric stimulation to the affected side | | | | | | | | | | | | | | | |
| | Nerve injury site | | | | Area surrounding nerve injury site | | | | Site compensating for the function of nerve injury site | | | | Whole-body exercise | | | |
| | Culture supernatant | | | | | | | | | | | | | | | |
| | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | B | B | B | B | B | B | B | B | B | B | B | B | C | C | C | C |
| 30 minutes after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | B | B | B | B | B | B | B | B | B | B | B | B | C | C | C | C |
| 20 hours after administration | C | C | C | C | C | C | C | C | C | C | C | C | — | — | — | — |

TABLE 4

| Nasal administration | Magnetic stimulation to the affected side | | | | | | | | | | | | | | | |
| | Nerve injury site | | | | Area surrounding nerve injury site | | | | Site compensating for the function of nerve injury site | | | | Whole-body exercise | | | |
| | Culture supernatant | | | | | | | | | | | | | | | |
| | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | B | B | B | B | B | B | B | B | B | B | B | B | C | C | C | C |
| 30 minutes after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | B | B | B | B | B | B | B | B | B | B | B | B | C | C | C | C |
| 20 hours after administration | C | C | C | C | C | C | C | C | C | C | C | C | — | — | — | — |

TABLE 5

| Nasal administration | Verbal stimulation | | | | Higher brain function stimulation | | | | Reference test (radio) | | | | Reference test (TV) | | | |
| | Culture supernatant | | | | | | | | | | | | | | | |
| | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | C | C | C | C |
| 1 hour before administration | C | C | C | C | C | C | C | C | C | C | C | C | C | C | C | C |
| Immediately after administration | B | B | B | B | B | B | B | B | C | C | C | C | C | C | C | C |
| 30 minutes after administration | A | A | A | A | A | A | A | A | C | C | C | C | C | C | C | C |
| 3 hours after administration | A | A | A | A | A | A | A | A | C | C | C | C | C | C | C | C |
| 10 hours after administration | B | B | B | B | B | B | B | B | C | C | C | C | C | C | C | C |
| 20 hours after administration | C | C | C | C | C | C | C | C | D | D | D | D | D | D | D | D |

TABLE 6

| Intravenous | Motor stimulation | | | | | | | | | | | | | | | |
|---|---|---|---|---|---|---|---|---|---|---|---|---|---|---|---|---|
| | Nerve injury site | | | | Area surrounding nerve injury site | | | | Site compensating for the function of nerve injury site | | | | Whole-body exercise | | | |
| | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 5 hours after administration | C | C | C | C | C | C | C | C | C | C | C | C | — | — | — | — |

TABLE 7

| Intravenous | Sensory stimulation to the affected side | | | | | | | | | | | | | | | |
|---|---|---|---|---|---|---|---|---|---|---|---|---|---|---|---|---|
| | Nerve injury site | | | | Area surrounding nerve injury site | | | | Site compensating for the function of nerve injury site | | | | Whole-body exercise | | | |
| | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 5 hours after administration | C | C | C | C | C | C | C | C | C | C | C | C | — | — | — | — |

40

TABLE 8

| Intravenous | Electric stimulation to the affected side | | | | | | | | | | | | | | | |
|---|---|---|---|---|---|---|---|---|---|---|---|---|---|---|---|---|
| | Nerve injury site | | | | Area surrounding nerve injury site | | | | Site compensating for the function of nerve injury site | | | | Whole-body exercise | | | |
| | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 5 hours after administration | C | C | C | C | C | C | C | C | C | C | C | C | — | — | — | — |

TABLE 9

| | Magnetic stimulation to the affected side | | | | | | | | | | | | | | | |
| Intravenous | Nerve injury site | | | | Area surrounding nerve injury site | | | | Site compensating for the function of nerve injury site | | | | Whole-body exercise | | | |
| | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 5 hours after administration | C | C | C | C | C | C | C | C | C | C | C | C | — | — | — | — |

TABLE 10

| | Verbal stimulation | | | | Higher brain function stimulation | | | | Reference test (radio) | | | | Reference test (TV) | | | |
| Intravenous | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | 1 | 2 | 3 | 4 | 1 | 2 | 3 | 4 | C | C | C | C | C | C | C | C |
| 1 hour before administration | C | C | C | C | C | C | C | C | C | C | C | C | C | C | C | C |
| Immediately after administration | A | A | A | A | A | A | A | A | C | C | C | C | C | C | C | C |
| 3 hours after administration | A | A | A | A | A | A | A | A | C | C | C | C | C | C | C | C |
| 5 hours after administration | C | C | C | C | C | C | C | C | D | D | D | D | D | D | D | D |

TABLE 11

| | Motor stimulation | | | | | | | | | | | | | | | |
| Subcutaneous | Nerve injury site | | | | Area surrounding nerve injury site | | | | Site compensating for the function of nerve injury site | | | | Whole-body exercise | | | |
| | Culture supernatant | | | | | | | | | | | | | | | |
| administration | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | C | C | C | C | C | C | C | C | C | C | C | C | C | C | C | C |
| 20 hours after administration | C | C | C | C | C | C | C | C | C | C | C | C | — | — | — | — |

TABLE 12

| | Sensory stimulation to the affected side | | | | | | | | | | | | | | | |
| Subcutaneous administration | Nerve injury site | | | | Area surrounding nerve injury site | | | | Site compensating for the function of nerve injury site | | | | Whole-body exercise | | | |
| | | | | | | | | Culture supernatant | | | | | | | | |
| | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | C | C | C | C | C | C | C | C | C | C | C | C | C | C | C | C |
| 20 hours after administration | C | C | C | C | C | C | C | C | C | C | C | C | — | — | — | — |

TABLE 13

| | Electric stimulation to the affected side | | | | | | | | | | | | | | | |
| Subcutaneous administration | Nerve injury site | | | | Area surrounding nerve injury site | | | | Site compensating for the function of nerve injury site | | | | Whole-body exercise | | | |
| | | | | | | | | Culture supernatant | | | | | | | | |
| | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | C | C | C | C | C | C | C | C | C | C | C | C | C | C | C | C |
| 20 hours after administration | C | C | C | C | C | C | C | C | C | C | C | C | — | — | — | — |

TABLE 14

| | Magnetic stimulation to the affected side | | | | | | | | | | | | | | | |
| Subcutaneous administration | Nerve injury site | | | | Area surrounding nerve injury site | | | | Site compensating for the function of nerve injury site | | | | Whole-body exercise | | | |
| | | | | | | | | Culture supernatant | | | | | | | | |
| | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|
| 6 hours before administration | C | C | C | C | C | C | C | C | C | C | C | C | — | — | — | — |
| 1 hour before administration | C | C | C | C | C | C | C | C | C | C | C | C | C | C | C | C |
| Immediately after administration | A | A | A | A | A | A | A | A | A | A | A | A | C | C | C | C |
| 3 hours after administration | A | A | A | A | A | A | A | A | A | A | A | A | C | C | C | C |
| 10 hours after administration | C | C | C | C | C | C | C | C | C | C | C | C | C | C | C | C |
| 20 hours after administration | C | C | C | C | C | C | C | C | C | C | C | C | — | — | — | — |

TABLE 15

| Subcutaneous administration | Verbal stimulation | | | | Higher brain function stimulation | | | | Reference test (radio) | | | | Reference test (TV) | | | |
|---|---|---|---|---|---|---|---|---|---|---|---|---|---|---|---|---|
| | | | | | Culture supernatant | | | | | | | | | | | |
| | 1 | 2 | 3 | 4 | 1 | 2 | 3 | 4 | 1 | 2 | 3 | 4 | 1 | 2 | 3 | 4 |
| 6 hours before administration | C | C | C | C | C | C | C | C | C | C | C | C | C | C | C | C |
| 1 hour before administration | C | C | C | C | C | C | C | C | C | C | C | C | C | C | C | C |
| Immediately after administration | A | A | A | A | A | A | A | A | C | C | C | C | C | C | C | C |
| 3 hours after administration | A | A | A | A | A | A | A | A | C | C | C | C | C | C | C | C |
| 10 hours after administration | C | C | C | C | C | C | C | C | C | C | C | C | C | C | C | C |
| 20 hours after administration | C | C | C | C | C | C | C | C | D | D | D | D | D | D | D | D |

As described above, according to the therapeutic agents used by the methods satisfying the requirements of the present invention, a significant improvement in the symptoms of the nerve disorders was observed.

In each administration method, the culture supernatant obtained in the above <Preparing culture supernatant of mesenchymal stem cells> was diluted about 3 to 10 times with the medium used for cell culture, adjusted to have the same soluble solid content, and then administered, so that an improvement in the symptoms of the nerve disorder was observed in the same manner as described above. However, the effect was highest when the culture supernatant was not diluted. In addition, in instances where the culture supernatant was diluted, the lower the dilution ratio, the higher the effect.

When nasal administration was performed, and then stimulation was applied at a time point between 5 minutes and 30 minutes after nasal administration, the therapeutic effects tended to be high.

Further, although not shown in the data, when nasal administration was performed, magnetic stimulation was applied for 30 minutes in a decubitus position 5 minutes after nasal administration of the culture supernatant, and then motor stimulation was applied immediately after the stimulation, the therapeutic effect was particularly high regardless of the types of the culture supernatants.

When nasal administration was performed, the effect tended to be higher in cases where patients got some sleep during the treatment than in cases where patients got no sleep during the treatment, even if the intervals between administration and stimulation were the same. In such cases, the effect tended to be more effective when patients had fallen asleep within 1 hour after nasal administration than that when patients had fallen asleep over 1 hour or longer.

The invention claimed is:

1. A method of treatment for a nerve disorder of a subject in need thereof, wherein the method comprising:
administering to the subject an therapeutic agent comprising a culture supernatant of a mesenchymal stem cell and/or a cell capable of differentiating into a mesenchymal stem cell, and is used in combination with stimulation of a nerve of the subject,
preferentially applying the stimulation to one or more sites selected from the group consisting of a nerve injury site, an area surrounding the nerve injury site, and a site compensating for the function of the nerve injury site, and adjusting timing of applying the stimulation based on a route of administration of the therapeutic agent.

2. The method according to claim 1, wherein the stimulation is one or more kinds of stimulation selected from the group consisting of motor stimulation, sensory stimulation, electrical stimulation, magnetic stimulation, verbal stimulation, and higher brain function stimulation.

3. The method according to claim 1, wherein preferentially applying the stimulation to the one or more sites comprises applying the stimulation to the one or more sites to a greater degree relative to other sites of the subject.

4. The method according to claim 1, wherein preferentially applying the stimulation to the one or more sites comprises applying the stimulation to the one or more sites such that a blood flow rate and a metabolic rate of the one or more sites increase to a greater degree relative to other sites of the subject.

5. A method of treatment for a nerve disorder of a subject in need thereof, wherein the method comprising:
nasally administering to the subject an therapeutic agent comprising a culture supernatant of a mesenchymal stem cell and/or a cell capable of differentiating into a mesenchymal stem cell, and is used in combination with stimulation of a nerve of the subject, and
the stimulation is performed between before and 16 hours after administration of the therapeutic agent.

6. The method according to claim 5, wherein the stimulation is one or more kinds of stimulation selected from the group consisting of motor stimulation, sensory stimulation, electrical stimulation, magnetic stimulation, verbal stimulation, and higher brain function stimulation.

7. The method according to claim 5, wherein the culture supernatant is not diluted or concentrated in terms of soluble solid content.

8. The method according to claim 5, wherein a lyophilizate of the culture supernatant is dissolved and then used at the time of administration.

9. A method of treatment for a nerve disorder of a subject in need thereof, wherein the method comprising:
intravenously administering to the subject an therapeutic agent comprising a culture supernatant of a mesenchymal stem cell and/or a cell capable of differentiating into a mesenchymal stem cell, and is used in combination with stimulation of a nerve of the subject, and
the stimulation is performed between before and 3 hours after administration of the therapeutic agent.

10. The method according to claim 9, wherein the stimulation is one or more kinds of stimulation selected from the group consisting of motor stimulation, sensory stimulation, electrical stimulation, magnetic stimulation, verbal stimulation, and higher brain function stimulation.

11. The method according to claim 9, wherein the culture supernatant is not diluted or concentrated in terms of soluble solid content.

12. The method according to claim 9, wherein a lyophilizate of the culture supernatant is dissolved and then used at the time of administration.

13. A method of treatment for a nerve disorder of a subject in need thereof, wherein the method comprising:

subcutaneously administering to the subject an therapeutic agent comprising a culture supernatant of a mesenchymal stem cell and/or a cell capable of differentiating into a mesenchymal stem cell, and is used in combination with stimulation of a nerve of the subject, and the stimulation is performed between before and 16 hours after administration of the therapeutic agent.

14. The method according to claim 13, wherein the stimulation is one or more kinds of stimulation selected from the group consisting of motor stimulation, sensory stimulation, electrical stimulation, magnetic stimulation, verbal stimulation, and higher brain function stimulation.

15. The method according to claim 13, wherein the culture supernatant is not diluted or concentrated in terms of soluble solid content.

16. The method according to claim 13, wherein a lyophilizate of the culture supernatant is dissolved and then used at the time of administration.

17. A method of treatment for a nerve disorder of a subject in need thereof, wherein the method comprising:

administering to the subject an therapeutic agent comprising a culture supernatant of a mesenchymal stem cell and/or a cell capable of differentiating into a mesenchymal stem cell, and is used in combination with stimulation of a nerve of the subject, and the stimulation is preferentially applied to one or more sites selected from the group consisting of a nerve injury site, an area surrounding the nerve injury site, and a site compensating for the function of the nerve injury site, wherein the culture supernatant is not diluted or concentrated in terms of soluble solid content.

18. A method of treatment for a nerve disorder of a subject in need thereof, wherein the method comprising:

administering to the subject an therapeutic agent comprising a culture supernatant of a mesenchymal stem cell and/or a cell capable of differentiating into a mesenchymal stem cell, and is used in combination with stimulation of a nerve of the subject, and the stimulation is preferentially applied to one or more sites selected from the group consisting of a nerve injury site, an area surrounding the nerve injury site, and a site compensating for the function of the nerve injury site, wherein a lyophilizate of the culture supernatant is dissolved and then used at the time of administration.

\* \* \* \* \*